United States Patent [19]

Humphlett et al.

[11] 4,168,169

[45] Sep. 18, 1979

[54] DRY HEAT-ACTIVATED BLEACHING OF SILVER IMAGES

[75] Inventors: Wilbert J. Humphlett; Rowland G. Mowrey, both of Rochester, N.Y.

[73] Assignee: Eastman Kodak Company, Rochester, N.Y.

[21] Appl. No.: 878,978

[22] Filed: Feb. 17, 1978

Related U.S. Application Data

[63] Continuation-in-part of Ser. No. 662,404, Mar. 1, 1976, abandoned.

[51] Int. Cl.² .......................... G03C 7/00; G03C 1/76; G03C 1/02
[52] U.S. Cl. ........................... 96/53; 96/50 R; 96/66 T; 96/73; 96/114.1
[58] Field of Search ................ 96/50 R, 76 R, 53, 73, 96/114.1, 95, 66 T; 526/2, 3, 5; 427/145; 428/199, 480, 483

[56] References Cited

U.S. PATENT DOCUMENTS

| | | | |
|---|---|---|---|
| 3,347,675 | 10/1967 | Henn et al. | 96/50 R |
| 3,414,411 | 12/1968 | Michel et al. | 46/53 |
| 3,493,372 | 2/1970 | Gompf et al. | 96/73 |
| 3,647,440 | 3/1972 | Rasch | 96/76 R |
| 3,708,300 | 1/1973 | Luckey | 96/73 |
| 3,745,009 | 7/1973 | Jenkins | 96/114.1 |
| 3,893,859 | 7/1975 | Burness | 96/61 R |
| 3,930,859 | 1/1976 | Corrigan | 96/76 R |

*Primary Examiner*—Mary F. Kelley
*Attorney, Agent, or Firm*—Richard E. Knapp

[57] ABSTRACT

A dry, activator sheet for a dry, thermal silver dye bleach process comprises a support having thereon a non-volatile, diffusible acid, a substituted heterocyclic thiazoline, oxazoline, imidazoline or imidazolidine silver halide complexing agent and a non-hydrolyzable polymer vehicle having an effective pH up to 6.0 and a melting point lower than 200° C. The activating sheet is useful to bleach a silver image containing a bleachable dye.

24 Claims, No Drawings

DRY HEAT-ACTIVATED BLEACHING OF SILVER IMAGES

This is a continuation-in-part application of U.S. Ser. No. 662,404 of W. J. Humphlett and R. G. Mowrey, filed March 1, 1976 now abandoned.

This invention relates to dry, activator sheets for use in bleaching photographic elements containing a silver image and a bleachable dye and to photographic elements and processes for bleaching silver images and dyes.

Many methods to produce positive color images with photographic silver halide materials have been described in the art. Those which are successfully employed in today's color photographic art include the silver-dye bleach process, as described, for example, in J. S. Friedman, *History of Color Photography*, (1944) pp. 405–429 and A. Meyer, *The Journal of Photographic Science*, Vol. 13, 90–97 (1965) and "The Theory of the Photographic Process", edited by T. H. James, Fourth Edition, 1977, pages 363–366; the color imaging process, as described in U.S. Pat. No. 2,252,718; and reversal processes which utilize the color development of photographic silver halide elements containing incorporated color-forming couplers, as described, for example, in U.S. Pat. Nos. 2,944,900; 2,984,567 and 3,189,452. In each of these processes, however, lengthy solution processing techniques are required which rely heavily on precision control and sophisticated techniques in order to produce color photographic images of high quality.

The silver dye bleach process involves developing a silver image in an exposed silver halide emulsion containing bleachable dye, and subsequently bleaching the dye in those areas where the silver has been developed. All the silver ion is removed or rendered transparent and insensitive to light by the bleach action, leaving a positive dye image in the areas where no metallic silver was present.

In most color photographic processes utilizing the above silver dye bleach system, it has been necessary to subject the exposed film to a large number of processing baths to achieve the discernable image. The exposed element is first developed with a black-and-white developer solution to produce a metallic silver image containing overall dye and then subjected to a strongly acidic dye bleach bath which decolorizes the dye in just those areas where the developed silver is present. The residual silver and silver halide are then removed in a subsequent bleach and fix bath and a direct-positive color image is obtained.

Photothermographic elements, i.e., photographic elements which produce a silver image upon imagewise exposure and then heat development are especially useful according to the invention. Examples of useful photothermographic elements that are useful according to the invention are described, for example, in Evans and McLaen U.S. Pat. No. 3,801,321 issued Apr. 2, 1974; Sullivan, Cole and Humphlett, U.S. Pat. No. 3,785,830 issued Jan. 15, 1974; and Haist et al, U.S. Pat. Nos. 3,301,678 and 3,531,285. These elements are particularly desirable in that an image can be produced by a dry process.

Michel et al., U.S. Pat. No. 3,414,411, issued Dec. 3, 1968, discloses an "in-camera" type system employing a photographic element comprising a support having thereon a silver halide emulsion containing the salt of an acid and a developed silver image having in association therewith a bleachable dye, or dye precursor. The exposed emulsion is contacted with a viscous alkaline processing solution and with a web having an acidic substituent which is capable of exchanging hydrogen ion with the cation of the salt of an acid which is present in the emulsion to lower the pH of the emulsion to a level at which imagewise bleaching of the dye in areas of metallic silver and in the presence of a silver complexing agent proceeds. The dye bleaching is described as being conducted in the presence of a catalyst and the web is delaminated to uncover the image.

The processing solution of Michel et al., U.S. Pat. No. 3,414,411, however, requires the use of salts which upon drying render the coating opaque due to crystallization and the web must be delaminated from the element for viewing purposes. The acid used in the processing web is non-diffusible and immobile. Thus, in order to bleach the silver metal, ion exchange must take place and the web must be peeled apart from the element.

The use of conventional dye bleach solutions is in some ways undesirable in that it is difficult to control the composition of the solution and the process is time consuming.

In copending U.S. Application Ser. No. 662,403 entitled "Dry Heat-Activated Bleaching of Silver Images" filed Mar. 1, 1976 by Mowrey and Oftedahl, an element comprising a silver image and bleachable dye is transferred into a positive colored dye image in the absence of solutions by contacting the element in the presence of heat with an activator sheet comprising a support having thereon a layer or layers comprising a diffusible acid and a non-hydrolyzable polymeric vehicle and containing a silver halide complexing agent such as thiourea.

It has been found, however, that the extended keeping of the activator sheets is hampered by the oxidation of the thiourea complexing agents. Thus, on keeping of the acidic activator sheets containing complexing agents such as thiourea the silver metal is effectively bleached but on keeping the activator may lose its ability to bleach the dye while continuing to bleach the silver image. Ultimately there may be a total loss of image discrimination.

It is desirable to provide an activator sheet containing a complexing agent with improved keeping properties.

SUMMARY OF THE INVENTION

It has been found according to the invention that an element comprising a silver image and at least one overall bleachable dye can provide a positive dye image in the absence of solutions by contacting the element at moderately elevated temperatures, e.g. about 50° C. to about 150° C., with a dry, activator sheet comprising a support having thereon a layer or layers comprising a non-volatile, diffusible acid and a non-hydrolyzable polymeric vehicle wherein the activator sheet has an effective pH of up to 6.0, preferably up to 4.0, in the absence of a silver dye-bleach catalyst, and is solid up to at least about 50° C. with a melting point lower than 200° C., said activator sheet comprising a silver halide complexing agent as described herein, preferably a substituted heterocyclic thiazoline, oxazoline, imidazoline or imidazolidine silver halide complexing agent.

In one embodiment of the invention, a dry, activator sheet for a dry, thermal silver-dye bleach process comprises a support having thereon,
(a) a non-volatile, diffusible acid selected from the group consisting of non-volatile, diffusible mineral acids and organic acids containing up to 10 carbon atoms, (b) a silver halide complexing agent comprising a substituted heterocyclic thiazoline, oxazoline, imidazoline or imidazolidine, and (c) a non-hydrolyzable polymeric vehicle, wherein said layer or layers has an effective pH of up to 6.0, preferably up to 4.0 in the absence of a silver dye-bleach catalyst, and is solid up to at least 50° C. with a melting point lower than 200° C.

In another embodiment, this invention also relates to a process of dye bleaching a photographic element comprising a silver image in association with at least one overall bleachable dye, such as a bleachable azo dye, by contacting the image, at moderately elevated temperatures, with a dry, activator layer comprising (a) a non-volatile, diffusible acid selected from the group consisting of non-volatile, diffusible mineral acids and organic acids containing up to 10 carbon atoms, (b) a silver halide complexing agent comprising a substituted heterocyclic thiazoline, oxazoline, imidazoline or imidazolidine, and (c) a non-hydrolyzable polymeric vehicle, wherein said layer or layers has a pH of up to 6.0, preferably up to 4.0 in the absence of a silver dye-bleach catalyst, and is solid up to at least 50° C. with a melting point lower than 200° C.

In still a further embodiment a dry, photographic element comprises a support having thereon a first layer containing a silver metal image and at least one overall bleachable dye, such as a bleachable azo dye, and laminated to the first layer a transparent second layer comprising (a) a non-volatile, diffusible acid selected from the group consisting of non-volatile, diffusible mineral acids and organic acids containing up to 10 carbon atoms, (b) a silver halide complexing agent comprising a substituted heterocyclic compound having the structure

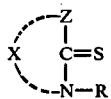

wherein X, which can be aryl-substituted or can be fused to an aryl group, represents the atoms necessary to complete a 5-membered heterocyclic ring, which can be unsaturated or saturated; X preferably contains only carbon atoms and the heterocyclic ring can be, for example, thiazoline, oxazoline, imidazoline, imidazolidine and the like; and Z is S, O or $NR^1$ wherein R and $R^1$ are independently selected from the group consisting of aliphatic and aromatic radicals and (c) a non-hydrolyzable polymeric vehicle wherein said second layer has an effective pH of up to 6.0, preferably up to 4.0 in the absence of a silver dye-bleach catalyst, and is solid up to at least 50° C. with a melting point lower than 200° C.

The activator sheet described herein is stable in the dry condition and can be kept on a shelf for long periods of time prior to use.

DETAILED DESCRIPTION OF THE INVENTION

The activator sheet useful to bleach a silver image in association with bleachable dyes comprises a support having thereon a layer or layers comprising (a) a non-volatile, diffusible acid selected from the group consisting of non-volatile, diffusible mineral acids containing up to 10 carbon atoms, (b) a substituted heterocyclic compound having the structure

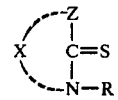

wherein X, Z, R, and $R^1$ are as described, and (c) a non-hydrolyzable polymeric vehicle wherein said layer or layers has an effective pH of up to 6.0, preferably up to 4.0 in the absence of a silver dye-bleach catalyst, and is solid up to at least 50° C. with a melting point lower than 200° C.

The term "dry" as used herein is intended to refer to materials that are dry to the touch. A dry activator sheet, for example, is dry to the touch as used herein. The activator sheet according to the invention can contain a concentration of atmospheric moisture which does not adversely effect the desired dye-bleach process. Also, the described photographic elements can contain a small concentration of moisture, but are dry to the touch. The activator sheet, as described, should neither contain water of hydration nor a concentration of water that is susceptible to vaporization during processing and formation of bubble defects. If an undesired concentration of moisture is present in the activator sheet prior to processing, this moisture should be removed prior to processing, such as by peheating the activator sheet.

The support for the activator sheet or web can be any material which retains dimensional stability at bleaching temperatures. Examples of suitable supports are paper, polyolefins such as polyethylene or polypropylene, polycarbonate, high temperature-resistant film supports such as supports from 1,1,3-trimethyl-5carboxy-3-(p-carboxyphenyl)indan polymers, cellulose acetate butyrate, poly(ethylene terephthalate), and the like. The preferred support materials are those which are translucent or transparent so that the positive color image can be viewed through the activator sheet.

The support has thereon either in a layer or layers the non-volatile, diffusible acid and the polymeric vehicle. The support and layer or layers containing the above substituents can also be separated by an intermediate layer such as a timing layer, for example, as a $TiO_2$ layer which would allow the silver image to be heat developed and bleached in a single heating step. The timing layer allows the development of the silver image prior to the bleaching by the activator sheet.

The acid used must be diffusible and mobile in the photographic laminate comprising the described activator sheet and photographic element so that the silver image can be effectively bleached in a short period of time. The acid can be selected from the group consisting of non-volatile, diffusible mineral acids and organic acids containing up to 10 carbon atoms. Each of these acids is useful providing that the processing temperature is lower than that which can vaporize the acid from the described sheet, but high enough to allow migration of the acid to the photographic element.

Mineral acids useful herein include sulfuric acid, sulfamic acid, phosphoric acid, and the like.

Examples of non-volatile, diffusible organic acids useful herein are those acids containing up to 10 carbon atoms including carboxylic acids such as citric acid, acetic acid and other acids such as p-toluenesulfonic acid, phenylphosphoric acid, phenylphosphinic acid, phenylphosphonic acid, benzenesulfonic acid, p-toluenesulfinic acid, and the like. Para-toluenesulfonic acid is especially useful.

It is important that the described mineral acids and organic acids be non-volatile to help avoid release of undesired products from the activator sheet or element according to the invention, especially at processing equipment. The term "non-volatile" as used herein is intended to mean that no significant concentration of acid, as described, is vaporized from the activator sheet or element according to the invention at processing temperature. For example, para-toluenesulfonic acid is a non-volatile acid within the invention because of significant concentration of this acid is measurable near the surface of an activator sheet or element according to the invention at processing temperature. Non-volatile acids useful in the practice of the invention can be selected based, in part, on the boiling point of the acids provided in, for instance, Tables of Physical Constants of Inorganic and Organic Compounds, *Handbook of Chemistry and Physics*, 57th Edition, CRC Press, 1976–1977.

It is critical that the acid be diffusible. By the term "diffusible acids" it is meant that the acids in themselves are mobile within the photographic laminant at the processing temperatures employed or they can be rendered mobile by the use of a suitable thermal solvent.

The acid incorporated in the activator sheet is generally strongly acidic and/or present in sufficient proportions to provide an effective pH of up to 6.0, preferably up to 4.0, in the layer or layers on the support. Acids which are unable, even at large portions, to reduce the effective pH in the layer or layers to a value below 6.0 would not be suitable for use according to the invention. In the absence of a silver dye-bleach catalyst, those acids which are unable to reduce the effective pH to 4.0 or less would not be suitable.

The term "effective pH" is intended herein to mean that the concentration of the described non-volatile, diffusible acid in the activator sheet, as described, is sufficient, at the described processing temperature, to enable the desired silver dye-bleach reaction to occur. Each of the examples that illustrate the invention in the following description have an "effective pH" within the desired range. The desired pH within the activator sheet can be determined by pH measurement techniques known in the chemical analytical art. For instance, a certain size sample of an activator sheet, as described, can be immersed in a certain quantity of water and the pH measured with a pH measuring apparatus known in the chemical art. In situations in which this is not convenient or suitable, a simple, acid concentration, test series can be carried out in which the concentration of non-volatile, diffusible acid is varied in the activator sheet according to the invention until the desired concentration is reached which produces the desired silver dye-bleach reaction at processing temperature. Also, another method which can be useful comprises placing a drop of water on the surface of the activator sheet according to the invention and measuring the pH at the surface of the sheet with a known pH measuring apparatus with an electrode designed to measure surface pH. In many instances, this latter method is most convenient.

The polymeric vehicle useful in this invention is a film-forming polymeric material containing organic residues which are non-hydrolyzable or slow to hydrolyze such as poly(vinyl alcohol), poly(acrylic acid), poly(styrenesulfonic acid), poly(vinylpyrrolidone), poly(ethylene oxide), and the like. It is critical that the vehicle be non-hydrolyzable or slow to hydrolyze because hydrolyzable vehicles such as gelatin compete for hydrogen ions and become hydrolyzed and denatured by the presence of the acid in the layer. The resulting layers then would be effective for only a short period of time after coating.

By the term "non-hydrolyzable vehicle" it is meant that a coating containing said vehicle and said diffusible acid when kept at room temperature, for instance about 24° C., and 50% relative humidity for about 4 weeks, shows no appreciable loss in activity due to pH changes caused by, for example, transesterification or transamidation reactions.

Examples of non-hydrolyzable vehicles useful herein are sulfonated polystyrene, poly(acrylic acid), poly(acrylamide), poly(vinyl alcohol), poly(vinylpyrrolidone), poly(ethylene oxide), and active methylene containing polymers such as copolymers of acrylamide and ethyl 5-(m- and p-vinylbenzyl)-3-oxo-pentanoate, copolymers of acrylamide and 6-(m- and p-vinylbenzyl)-2,4-hexanedione and the like. Poly(vinylpyrrolidone) is especially useful.

The preferred complexing agents have the structure

wherein X, which can be aryl-substituted or can be fused to an aryl group, represents the atoms necessary to close a 5-membered heterocylic ring which can be unsaturated or saturated; X preferably contains only carbon atoms and the heterocyclic ring can be, for example, thiazoline, oxazoline, imidazoline, imidazolidine and the like. It is preferred that if X is aryl-substituted or fused to an aryl group, the aryl group contain from 6 to 10 carbon atoms such as phenyl. Z is S, O or $NR^1$. R and $R^1$ are independently selected from the group consisting of aliphatic and aromatic radicals which do not adversely affect the desired bleaching process, such as alkyl containing from 1 to 4 carbon atoms such as methyl, ethyl, propyl, isobutyl and the like including substituted alkyl such as alkyls containing a terminal acidic hydrogen atom bonded to an oxygen atom such as carboxyalkyl, sulfoalkyl and the like, preferably containing from 1 to 12 carbon atoms and the salts thereof, alkyl aryl keto groups containing up to 15 carbon atoms and preferably up to 9 carbon atoms such as

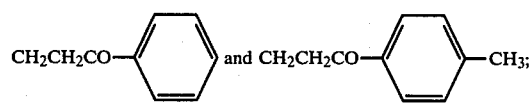

an aliphatic keto group containing up to 8 carbon atoms such as $CH_2CH_2COOCH_3$ and $CH_2CH_2COC_2H_5$; aliphatic esters of aliphatic carboxylic acid groups containing up to 11 carbon atoms such as $CH_2CH_2CO_2CH_3$ and $CH_2CH_2CO_2C_2H_5$; cyanoethyl groups containing up to 3 carbon atoms such as $CH_2CH_2CN$; or sulfoalkyl groups or salts thereof such as $CH_2CH_2SO_3K$.

The silver halide complexing agent particularly useful herein is a substituted heterocyclic thiazoline, oxazoline, imidazoline or imidazolidine. The use of the substituted heterocyclic thiazoline, oxazoline, imidazoline or imidazolidine as a complexing agent shows unexpectedly improved keeping properties in comparison, for instance, to the use of thiourea as described in the copending U.S. Application Ser. No. 662,403 filed Mar. 1, 1976 by Mowrey and Oftedahl described above.

It is noted that although R and $R^1$ can be any aliphatic or aromatic radical which does not adversely affect the desired bleaching, neither can be terminated with an alcoholic OH group. It is also further noted that the complexing agent should contain a total of 20 carbon atoms or less.

Especially preferred complexing agents have the structures:

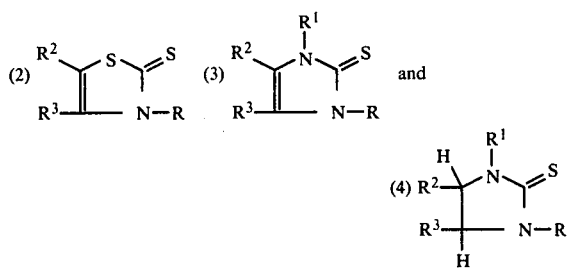

wherein R and $R^1$ are as defined and $R^2$ and $R^3$ each represent a member selected from the group consisting of hydrogen and aliphatic radicals which do not adversely affect the desired bleaching, such as alkyl containing up to 8 carbon atoms, e.g., methyl, ethyl, octyl and the like; aryl such as phenyl and $R^2$ and $R^3$ can together form a 6 to 10 carbon atom containing aromatic ring such as phenyl or the like or a 5 to 7 member alicyclic ring such as cyclopentyl, cyclohexyl, methylcyclohexyl, cycloheptyl and the like. R and $R^1$ in above structures (2), (3) and (4) are typically independently selected from aliphatic radicals containing from 1 to 12 carbon atoms which have a terminal acidic hydrogenation bonded to an oxygen atom and salts thereof.

Some especially preferred specific compounds corresponding to the above structure (1) include:
(1) 3-Carboxymethyl-4-methyl-4-thiazoline-2-thione;
(2) 3-(2-Carboxyethyl)-4-methyl-4-thiazoline-2-thione;
(3) 3-(1,2-Dicarboxyethyl)-4-methyl-4-thiazoline-2-thione;
(4) 4-Methyl-3-(2-sulfoethyl)-4-thiazoline-2-thione potassium salt;
(5) 3-(1-Carboxyethyl)-4-methyl-4-thiazoline-2-thione;
(6) 3-(1-Carboxy-3-methylthiopropyl)-4-methyl-4-thiazoline-2-thione;
(7) 4-Carboxy-3-(1-carboxyethyl)-4-thiazoline-2-thione;
(8) 1,3-Dimethylimidazoline-2-thione;
(9) 1,3-Dimethylimidazolidine-2-thione.

The described dry activator sheet or elements can contain one or more of the complexing agents.

Examples of syntheses of thiazoline, imidazoline and imidazolidine thiones are described respectively in *J. Heterocyclic Chem.*, 4, 605 (1967); *C. R. Acad. Sc. Paris*, 276, Series C, 653 (1973); and *J. Organometal Chem.*, 50, 113 (1973).

Syntheses of 4-thiazoline-2-thiones bearing a carboxy group in the 3-position also has been described in *Berichte*, 56, 289 (1923); *Compt. rend. trav. lab. Carlsberg, Ser.Chim.*, 22, 211 (1938); C. A., 32, 6246[3] (1938); *Journal Am. Chem. Soc.*, 72, 1879 (1950). These syntheses involve treating a dithiocarbamic acid derived from an amino acid and carbon disulfide with an α-halogenated ketone. The earlier published procedures can be slightly modified by employing methanol instead of water as solvent and by using two equivalents of amino acid and carbon disulfide per equivalent of α-halo ketones. In some instances, depending on reaction conditions, an intermediate reaction product, either a 4-hydroxy-thiazolidine-2-thione or a dithiocarbamate is obtained which can then be dehydrated or cyclodehydrated to the 3-substituted-4-thiazoline-2-thione. We have prepared a variety of 3-substituted-4-thiazoline-2-thiones using amino acids such as glycine; D,L- or β-alanine; 4-aminobutyric acid; DL-aspartic acid; taurine; D,L methionine; 6-aminohexanoic acid and m-aminobenzoic acid and employing such α-halo ketones as chloroacetone; phenacyl bromide; 3-chloro-2-butanone; ethyl bromopyruvate; ethyl 2- and 4-chloroacetoacetate; 1-acetoxy-3-chloro-2-propanone; 1-butylsulfonyl-3-bromo-2-propanone and 3-chloro-2,4-pentanedione.

The following syntheses typify preferred procedures for preparing certain 3-substituted-4-thiazoline-2-thiones.

A.
4-Acetoxymethyl-3-(2-carboxyethyl)-4-thiazoline-2-thione

A mixture of 55.2 grams (0.62 mole) of D,L-alanine and 36.8 grams (0.56 mole) of potassium hydroxide in 150 milliliters of methanol is made with warming and stirring. To the stirred mixture cooled in an ice bath is added 34 milliliters (0.56 mole) of carbon disulfide over 20 minutes, forming a gummy, white solid. After the cooled mixture is stirred for one hour, a solution of 42 grams (0.28 mole) of 1-acetoxy-3-chloro-2-propanone in an equal volume of methanol is added, with cooling and stirring, over 20 minutes. The reaction mixture is stirred for 1 hour, with cooling. The reactions are exothermic. Sufficient water, about 200 milliliters, to form a solution is added, and the solution is stirred 15 minutes longer. Methanol is removed in vacuo, leaving a yellow solution. Acidification with excess concentrated hydrochloric acid causes an oil to separate which solidifies on standing overnight. Filtration yields 66 grams of crude product, m.p. 144° C. Pure product is obtained after two recrystallizations, amounting to 46 grams of light tan needles.

B. 3-(2-Carboxyethyl)-4-phenyl-4-thiazoline-2-thione

A solution of 10 grams (0.035 mole) of 3-(2-carboxyethyl)-4-hydroxy-4-phenylthiazolidine-2-thione in 50 milliliters of glacial acetic acid is refluxed for 0.5 hour. On cooling, crystals form as prisms. Water (100 milliliters) is added, and the crystals are collected, giving 7 grams of the thiazoline, m.p. 134°-136° C. A second crop gives 2.5 grams.

Table I describes examples of 3-substituted-4-thiazoline-2-thiones derived from amino acids by such procedures:

TABLE I 4-thiazoline-2-thiones derived from amino acids $$\begin{array}{c} R^2\diagdown_{C}\diagup^{S}\diagdown_{C}\!=\!S \\ \| \quad \quad \| \\ R^3\diagup^{C}\!\!-\!\!N\!-\!R \end{array}$$

| R | $R^3$ | $R^2$ | Formula | M.P. °C.[a] |
|---|---|---|---|---|
| $CH_2CO_2H$ | $CH_2CO_2C_2H_5$ | H | $C_9H_{11}NO_4S_2$ | 142–143 |
| $CH_2CO_2H$ | $CH_2CO_2H$ | H | $C_7H_7NO_4S_2$ | 175–176 |
| $CH_2CO_2H$ | $CH_2OCOCH_3$ | H | $C_8H_9NO_4S_2$ | 162–163 |
| $CH_2CO_2H$ | $CH_3$ | $CO_2C_2H_5$ | $C_9H_{11}NO_4S_2$ | 159–160 |
| $CH_2CO_2H$ | $CH_3$ | $CO_2H$ | $C_7H_7NO_4S_2$ | 224–225 |
| $CH_2CO_2H$ | $CH_3$ | $COCH_3$ | $C_8H_9NO_3S_2$ | 184–185 |
| $(CH_2)_2CO_2H$ | H | H | $C_6H_7NO_2S_2 \cdot H_2O$ | 58–60 |
| $(CH_2)_2CO_2H$ | $CH_3$ | H | $C_7H_9NO_2S_2$ | 132–134 |
| $(CH_2)_2CO_2H$ | $CH_2OCOCH_3$ | H | $C_9H_{11}NO_4S_2$ | 153 |
| $(CH_2)_2CO_2H$ | $CH_2OH$ | H | $C_7H_9NO_3S_2$ | 141 |
| $(CH_2)_2CO_2H$ | $CH_2SO_2C_4H_9$ | H | $C_{11}H_{17}NO_4S_3$ | 137–138 |
| $(CH_2)_2CO_2H$ | $C_6H_5$ | H | $C_{12}H_{11}NO_2S_2$ | [b]136–137 |
| $(CH_2)_2CO_2H$ | $CH_3$ | $COCH_3$ | $C_9H_{11}NO_3S_2$ | 142–143 |
| $(CH_2)_2CO_2H$ | $CH_3$ | $CO_2C_2H_5$ | $C_{10}H_{13}NO_4S_2$ | 145–146 |
| $(CH_2)_2CO_2H$ | $CH_3$ | $CO_2H$ | $C_8H_9NO_4S_2$ | 206–207 |
| $CH(CH_3)CO_2H$ | H | H | $C_6H_7NO_2S_2$ | 146–148 |
| $CH(CH_3)CO_2H$ | $CO_2C_2H_5$ | H | $C_9H_{11}NO_4S_2$ | 194 |
| $CH(CH_3)CO_2H$ | $CO_2H$ | H | $C_7H_7NO_4S_2$ | 212 |
| $CH(CH_3)CO_2H$ | $CH_2CO_2C_2H_5$ | H | $C_{10}H_{14}NO_4S_2$ | 60–61 |
| $CH(CH_3)CO_2H$ | $CH_2CO_2K$ | H | $C_8H_8KNO_4S_2$ | 232 |
| $CH(CH_3)CO_2H$ | $CH_3$ | $COCH_3$ | $C_9H_{11}NO_3S_2$ | 136–137 |
| $(CH_2)_3CO_2H$ | $CH_2CO_2C_2H_5$ | H | $C_{11}H_{15}NO_4S_2$ | 100–101 |
| $(CH_2)_3CO_2H$ | $CH_2CO_2H$ | H | $C_9H_{11}NO_4S_2$ | 147–148 |
| $(CH_2)_3CO_2H$ | $CH_2SO_2C_4H_9$ | H | $C_{12}H_{19}NO_4S_3$ | 145–146 |
| $(CH_2)_3CO_2H$ | $C_6H_5$ | H | $C_{13}H_{13}NO_2S_2$ | 137–138 |
| $(CH_2)_3CO_2H$ | $CH_3$ | $CO_2C_2H_5$ | $C_{11}H_{15}NO_4S_2$ | 122–123 |
| $(CH_2)_3CO_2H$ | $CH_3$ | $CO_2H$ | $C_9H_{11}NO_4S_2$ | 203 |
| $(CH_2)_5CO_2H$ | $CH_3$ | H | $C_{10}H_{15}NO_2S_2$ | 86–87 |
| $CHCO_2H$<br>\|<br>$CH_2CO_2H$ | $CH_3$ | H | $C_8H_9NO_4S_2$ | 217–218 |
| $CH_2CH_2SO_3K$ | $CH_3$ | H | $C_6H_8NO_3S_3K$ | [c]362 |
| $CH_3S(CH_2)_2CHCO_2H$ | $CH_3$ | H | $C_9N_{13}NO_2S_2$ | 130 |
| $C_6H_4CO_2H$-m | $CH_3$ | H | $C_{11}H_9NO_2S_2$ | [b]191–193 |

[a]Recrystallized from water unless otherwise indicated
[b]From 50% ethanol
[c]From methanol The activator sheet can also contain a thermal solvent, if desired, to aid the acid in diffusing to the emulsion layer. The thermal solvent should be added if the depressed melting point of the mixture of the diffusible acid and the complexing agent, if any, is 200° C. or higher. The thermal solvents can, at any rate, accelerate the rate of bleaching by depressing the melting point of the mixture.

The term "thermal solvent" as used herein means a non-hydrolyzable organic material which is a solid at ambient temperatures, such as about 24° C., but which has a mixed melting point with the other ingredients at or below the temperature of the thermal process employed. Preferred thermal solvents for this invention include a variety of ethers, sugars and alcohols which act as solvents for the incorporated materials functioning in the process.

Examples of useful thermal solvents can be found in U.S. Pat. No. 3,667,959 issued June 6, 1972; U.S. Pat. No. 3,347,675 issued Oct. 17, 1967 and U.S. Pat. No. 3,438,776 issued Apr. 15, 1969 and include non-hydrolyzable polar solvents containing up to 10 carbon atoms such as ethylene glycol, and low molecular weight poly(ethylene glycol) and poly(ethylene oxide), decanediol, hexanediol, sorbitol and the like.

If the effective pH of the activator sheet is higher than 4.0, in accordance with the invention, a silver dye-bleach catalyst must be incorporated in the photographic emulsion, the acidic activator sheet, or in both of these materials to aid in obtaining an optimum dye image. Advantageously, the bleaching of the image dye, when the effective pH is higher than 4.0 in the activator sheet, is conducted in the presence of a suitable silver dye-bleach catalyst, such as a phenazine, a quinoxaline, an anthraquinone, or a pyrazine. A number of catalysts useful herein are described in U.S. Pat. Nos. 2,183,395 and 2,270,118. These compounds oxidize the metallic silver to silver ion, and in so doing are reduced. The reduced catalyst then cross-oxidizes with the image dye. This cross-oxidation decolorizes, i.e. bleaches, the image dye and oxidizes the catalyst back to its original state.

If the activator sheet is at an effective pH of about 4.0 to about 6.0, a catalyst must be included in the activator sheet. If the pH of the activator sheet is 4.0 or lower, the use of a catalyst is optional.

Other addenda such as bleaching compounds, fixing compounds and activating compounds known in the art can be incorporated into the activator sheet of this invention.

In order to satisfactorily bleach out the silver image with a brief heating step the activator sheet must have an effective pH not greater than 6.0, preferably not greater than 4.0, and its melting point must be sufficiently low to enable the acid at processing temperatures to diffuse to the emulsion layer, i.e. a melting point below about 200° C., such as within the range of about 50° C. to about 150° C. Thus, the strength and proportion of the acid can be adjusted to achieve the low pH values and the use of the thermal solvent can lower the melting point of the activator material containing acids having higher melting points in order to achieve these properties.

It is pointed out that if gelatin is used as a binder in the emulsion layers, since it is a buffer, more acid should be used. Binders which are not buffers may require the use of less acid.

The acid component described can be present in any amount in the activator sheet so long as the effective pH of the layer or layers in the sheet is 6.0 or less, preferably 4.0 or less. Preferably the acid is present from about 1.0 g/m$^2$ to about 50 g/m$^2$ in the activator sheet. The polymeric vehicle preferably is present from about 1.0 g/m$^2$ to about 50 g/m$^2$ in the activator sheet. Typical concentrations for complexing agents are from about 1.0 g/m$^2$ to about 50 g/m$^2$ or about 1 mole to about 5 mole/mole of of AgX. Thermal solvents can be present from about 1.0 g/m$^2$ to about 50 g/m$^2$ while catalysts, such as phenazine, are present from about 0 to about 1.0 g/m$^2$ in the activator sheet.

The activator sheet can be prepared by coating onto a suitable support a coating composition comprising the acid, the vehicle, optionally the complexing agent, the thermal solvent, and, optionally, a catalyst, and then drying. The various components are coated from a solvent such as methanol, ethanol, acetone, water, or the like. The various components can be coated in different contiguous layers.

A typical dry, activator sheet or web comprises the following components:

| | |
|---|---|
| 3-carboxymethyl-4-methyl-4-thiazoline-2-thione (complexing agent) | 5.4 g/m$^2$ |
| 1,6-hexanediol (thermal solvent) | 5.4 g/m$^2$ |
| p-toluenesulfonic acid (acid) | 5.4 g/m$^2$ |
| poly(vinylpyrrolidone) (polymeric vehicle) | 2.7 g/m$^2$ |
| Triton TX-100 (Surfactant which is a sodium salt of an alkyl aryl polyether sulfonate) | 1.25 ml (10% solution) |
| in methanol/distilled water (50:50 parts by volume) | |

This activator sheet or web has an effective pH of less than 4.0.

The silver and dye images are bleached by merely placing the activator sheet over the image and laminating by applying heat at the melting point of the activator sheet and lightly pressing the two sheets together, such as with a roller or other suitable means. Excessive pressure in pressing the two sheets together should be avoided.

The element produced thereby is bleached to a positive dye image preferably by heating to a temperature of about 50° C. to about 150° C. and more preferably from about 90° C. to about 120° C. over a time period ranging from about 2 to about 300 seconds, preferably from about 15 to 30 seconds. The temperature and length of heating can be varied widely depending on the thickness of the emulsion, activator chemistry layers, desired image, and the like. Excessive pressure on the laminate during the described heating step is to be avoided. Undue pressure on the laminate during this step can provide less than an optimum dye image.

Any suitable means can be useful to provide the desired processing temperature. The heating means can be a simple hot plate, iron, roller, oven or the like.

Processing is usually carried out under atmospheric conditions of pressure and humidity.

In a preferred embodiment, the support for the activator sheet is transparent so that the image is visible through the activator sheet. It is a particular advantage of this invention that the activator sheet need not be delaminated from the image. The resulting photographic element comprises a support having thereon a first layer containing a silver metal image and overall bleachable dye (in both image and non-image areas) and laminated to the dye image a transparent second layer comprising (a) a non-volatile, diffusible acid selected from the group consisting of non-volatile, diffusible mineral acids and organic acids containing up to 10 carbon atoms, (b) a substituted heterocyclic silver halide complexing agent, as described, preferably a thiazoline, oxazoline, imidazoline or imidazolidine silver halide complexing agent, and (c) a non-hydrolyzable polymeric vehicle wherein said second layer or layers has an effective pH of up to 6.0, preferably up to 4.0 in the absence of a silver dye-bleach catalyst, and is solid up to at least 50° C. with a melting point lower than 200° C.

The photographic element can be prepared using any source for the silver image. For example, the silver image can be provided by imagewise exposing an emulsion containing a silver salt such as silver behenate, silver laurate, silver trifluoroacetate or silver halide such as silver chloride, silver chlorobromide, or the like and chemically developing or physically developing the image in a conventional developer bath or by heat if using a photothermographic element.

In yet another embodiment, a silver image with an overall dye covering can be obtained by simply depositing silver through a mask and overall depositing the bleachable dye.

The bleachable dyes used herein are well known in the art. The term "bleachable dyes" as used herein includes compounds which are dye precursors, i.e., colorless compounds which become colored during processing of the photographic materials and shifted dyes which shift hypsochromically or bathochromically to the desired image hues when subjected to a different environment such as a change in pH, reaction with a material to form a complex, etc. The term "non-diffusible" as used herein refers to bleachable dyes which in themselves are non-diffusible in the emulsion, or dyes which are rendered non-diffusible by the use of a suitable mordant, such as those described in U.S. Pat. No. 2,882,156. The elements of this invention can have a single emulsion coating for monochrome dye images formed from either one or a mixture of azo dyes, which dye images are either colored or neutral (e.g., black and white) images. Primarily, azo dyes are used in silver dye-bleach systems because the bleaching process cleaves the —N=N— double bond to give two aromatic fragments. Typical azo dyes which can be used in the practice of this invention are listed in numerous patents, some of which are U.K. Pat. Nos. 923,265; 999,996; 1,042,300; 1,077,628; and U.S. Pat. Nos. 3,178,290; 3,178,291; 3,183,225; and 3,211,556.

Bleachable dyes include those known in the art and dyes such as disclosed in the Color Index (third edition) published by the Society of Dyers and Colourists, copyright 1971, printed by Lund Humphreys, Bradford and London, provided they are bleachable as herein described. This includes bleachable dyes such as azo dyes, formazan dyes, azoxy dyes, xanthene dyes, azine dyes, phenylmethane dyes, nitroso dyes, indigo dyes, quinones, nitro-substituted dyes, phthalocyanines, and others known to one skilled in the art. Precursors to these dyes as known in the art, such as, hydrazo or diazonium compounds to yield azo dyes, tetrazolium salts to yield formazan dyes, etc., are also useful herein.

The bleachable dyes are defined as those dyes which in the presence of a photographic image comprised of silver metal and an aqueous solution of a silver complexing agent according to the invention, such as 3-carboxymethyl-4-methyl-4-thiazoline-2-thione, at an effective pH of up to 4.0 suffer discharge of their color proportionate to the amount of silver metal present. Further examples of these dyes may be found in U.S. Pat. Nos. 3,202,511 and 3,443,372 and U.K. Pat. Nos. 1,146,118 and 1,255,857.

The elements of this invention may have a plurality of coatings each containing a different bleachable dye for providing multicolor images. Especially useful arrangements are those in which at least three light-sensitive emulsion layers are provided which are respectively sensitized to blue, green and red radiation, and contain, respectively, non-diffusible yellow, magenta and cyan dyes. The emulsions used in this invention can contain the bleachable dyes. However, it is also possible, and sometimes preferable, to incorporate the bleachable dye in an alkaline-permeable layer contiguous to the emulsion layer. This arrangement provides increased speed, especially when the bleachable dye containing layer is coated under the emulsion layer. Thus, in one useful arrangement a support has coated thereon, in the following order, layers containing, respectively, blue-sensitive silver halide; bleachable yellow dye; green-sensitive silver halide; bleachable magenta dye; red-sensitive silver halide; and bleachable cyan dye.

The dyes can be added by any of the conventional methods known in the art, for example, as dispersions in which ballasted dyes are rendered partially soluble by use of a sulfonic acid or carboxylic acid substituent; or as dispersions wherein an oil soluble dye is dispersed alone or in the presence of a high boiling solvent in the photographic binder.

In the silver dye-bleach system, photographically developed silver is used to reduce a dye from a colored to a colorless form. This dye bleaching step is usually carried out in an acidic solution in the presence of a silver complexing agent and a dye bleach catalyst. In this invention, a dry sheet is provided to carry out the bleach step, preferably in the absence of a silver dye-bleach catalyst at an effective pH of up to 4.0.

In its most usual form, a dye-bleach system consists of a support coated with at least one silver halide emulsion layer containing a bleachable azo dye. After exposure the silver halide is developed to a negative silver image; during the dye-bleach step, a positive dye image is formed. This is usually followed by conventional silver bleaching and fixing.

The bleachable dyes are preferably used at a concentration ranging from about 0.1 g/m² to about 3.00 g/m² to achieve a discernible image, depending on the molar extinction coefficient of the dye, and whether a reflection print or transparency is desired.

In the preferred embodiment the photographic element is completely dry processed, i.e., in the absence of any processing solutions or baths. The silver image is produced by a photothermographic process using a photothermographic element.

Typical photothermographic elements to which the bleachable dyes are added are described in U.S. Pat. No. 3,785,830 of Sullivan, Cole and Humphlett; U.S. Pat. No. 3,301,678 and U.S. Pat. No. 3,531,285 both by Haist, Humphlett and Johnson; and U.S. Pat. No. 3,801,321 of Evans and Mclaen.

Other photothermographic elements which are processed by heat include those containing a silver salt and a base precursor such as trifluoroacetic acid, carboxylic acid amines, or bis-isothiuronium compounds such as those described in U.S. Pat. No. 3,669,670 of Haist and Humphlett.

The photothermographic element can comprise a support having thereon a reducing agent, a silver salt oxidizing agent, and a photosensitive silver halide composition. Typically, preferred photothermographic elements are described in U.S. Pat. Nos. 3,785,830; 3,801,321; 3,301,678 and 3,531,285.

Various reducing agents useful in photothermographic compositions containing bleachable dyes and optionally silver complexing agents are, for example, polyhydroxybenzenes such as hydroquinone developing agents including, for instance, hydroquinone, alkyl substituted hydroquinones, exemplified by tertiarybutylhydroquinone, methylhydroquinone, 2,5-dimethylhydroquinone and 2,6-dimethylhydroquinone; catechols and pyrogallol; halo-substituted hydroquinones such as chlorohydroquinone or dichlorohydroquinone; alkoxy substituted hydroquinones such as methoxyhydroquinone or ethoxyhydroquinone and the like. Other reducing agents which can be employed include reductone developing agents such as anhydro dihydro piperidino hexose reductone; hydroxytetronic acid reducing agents and hydroxytetronimide developing agents; 3-pyrazolidinone developing agents such as 1-phenyl-3-pyrazolidinone and 4-methyl-4-hydroxymethyl-1-phenyl-3-pyrazolidinone and those described in British Pat. No. 930,572 published July 3, 1963; certain hydroxylamine developing agents; ascorbic acid developing agents such as ascorbic acid, ascorbic acid ketals, and other ascorbic acid derivatives; phenylenediamine developing agents; certain aminophenol developing agents and the like. Combinations of reducing agents can also be employed. The preferred reducing agents are sulfonamidophenols such as 2,6-dichloro and 2,6-dibromo-4-benzenesulfonamidophenols as described in U.S. Pat. No. 3,801,321 and bis-beta naphthols such as described in U.S. Pat. No. 3,751,249.

The silver salt oxidizing agent can be a silver salt of a long-chain fatty acid such as silver behenate, silver stearate, silver oleate, silver laurate, silver hydroxystearate, silver caprate, silver myristate and silver palmitate as well as silver benzoate, silver phthalate, silver acetate, silver phthalazinone, silver benzotriazole and silver saccharin. A particularly useful silver salt herein is a silver salt of a thione. The silver salt of the thione can be prepared in situ in the photothermographic materials by combining a source of silver, such as silver trifluoroacetate, with the thione compound in the composition. The thione compound is a compound represented by the formula:

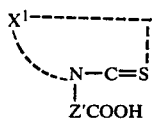

wherein $X^1$ represents atoms completing a 5 member heterocyclic nucleus, such as a thiazoline nucleus, and $Z'$ is alkylene, such as alkylene containing 1 to 30 carbon atoms, typically 1 to 10 carbon atoms. Examples of suitable 5 member heterocyclic nuclei are thiazoline-2-thione, benzothiazoline2-thione, imidazoline-2-thione or similar heterocyclic thione nucleus. The heterocyclic nucleus can contain substituent groups which do not adversely affect the described photothermographic materials or bleaching process, such as alkyl containing 1 to 3 carbon atoms, or phenyl. Alkylene as employed herein includes so-called branched chain alkylen such as

An especially suitable silver salt forming thione compound is a thiazoline-2-thione represented by the formula:

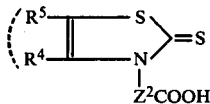

wherein $Z^2$ is alkylene containing 1 to 4 carbon atoms, typically methylene; $R^4$ and $R^5$ are each selected from the group consisting of hydrogen, alkyl containing 1 to 4 carbon atoms, and aryl containing 6 to 10 carbon atoms, or taken together are atoms completing a benzo group. The alkyl, aryl and benzo groups can be substituted with groups which do not adversely affect the described photothermographic materials or bleaching process, such as alkyl containing 1 to 3 carbon atoms, or phenyl.

Another suitable silver salt forming thione compound is an imidazoline-2-thione represented by the formula:

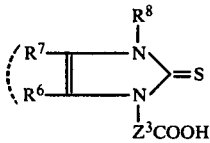

wherein $Z^3$ is alkylene containing 1 to 4 carbon atoms, typically ethylene; $R^8$ is alkyl, typically alkyl containing 1 to 3 carbon atoms, such as methyl, ethyl or propyl, aryl containing 6 to 10 carbon atoms, such as phenyl, or carboxyalkyl, such as carboxyethyl and carboxymethyl; $R^6$ and $R^7$ are each selected from the group consisting of hydrogen, alkyl containing 1 to 4 carbon atoms, such as methyl, ethyl and propyl, aryl containing 6 to 10 carbon atoms, such as phenyl or tolyl, or $R^4$ and $R^5$ taken together are atoms completing a benzo group.

A further suitable silver salt forming thione compound is an oxazoline-2-thione represented by the formula:

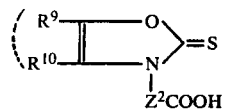

wherein $Z^2$ is as described; $R^9$ and $R^{10}$ are each selected from the group consisting of hydrogen, alkyl containing 1 to 4 carbon atoms, such as methyl, ethyl, and propyl, aryl containing 6 to 10 carbon atoms, such as phenyl or tolyl, or $R^9$ and $R^{10}$ taken together are atoms completing a benzo group.

Examples of suitable thione compounds within the described formulas include:
3-(2-carboxyethyl)-4-methyl-4-thiazoline-2-thione,
3-(2-carboxyethyl)benzothiazoline-2-thione,
3-(2-carboxyethyl)-5-phenyl-1,3,4-oxadiazoline-2-thione,
3-(2-carboxyethyl)-5-phenyl-1,3,4-thiadiazoline-2-thione,
3-(carboxymethyl)-4-methyl-4-thiazoline-2-thione,
3-(2-carboxyethyl)-1-phenyl-1,3,4-triazoline-2-thione,
1,3-bis(2-carboxyethyl)imidazoline-2-thione,
1,3-bis(2-carboxyethyl)benzimidazoline-2-thione,
3-(2-carboxyethyl)-1-methylimidazoline-2-thione,
3-(2-carboxyethyl)benzoxazoline-2-thione, and
3-(1-carboxyethyl)-4-methyl-4-thiazoline-2-thione.

The described thione compounds can be prepared employing processes known in the art. The described silver complexes of the thione compounds can be prepared in situ, as described, or the silver complexes can be isolated.

The photosensitive silver halide useful herein can include, for example, silver chloride, silver bromide, silver bromoiodide, silver chlorobromoiodide, or mixtures thereof. For the purposes of the invention, silver iodide is also included as a photosensitive silver halide. While the photosensitive silver halide can be prepared in situ in the photothermographic material, this is not necessary according to the invention. The photosensitive silver halide can be coarse or fine-grain, very fine-grain photosensitive silver halide being especially useful. The photosensitive silver halide can be prepared by any of the well-known procedures employed in the photographic art. The silver halide can be prepared, for example, employing single-jet preparation techniques, double-jet preparation techniques, such as techniques employed in preparing Lippmann emulsions and the like. Surface image or internal image silver halide materials can be used. If desired, mixtures of surface and internal image silver halide materials can be used. Negative type silver halide is typically employed. The silver halide materials can be regular grain such as described in Klein and Moisar, *Journal of Photographic Science*, Volume 12, No. 5, September-October (1964), pages 242–251.

The photosensitive silver halide can be chemically sensitized employing techniques known in the photographic art.

Although a binder is not essential with the photothermographic materials described, a binder is typically employed. The binders which are useful with the described photothermographic materials include various colloids employed alone or in combination as vehicles and/or binding agents which do not adversely affect the desired photothermographic properties of the described compositions and in various layers of a photothermographic element. Suitable materials can be hydrophilic or hydrophobic. The binders which are suitable are transparent or translucent and include both naturally-occurring substances such as proteins, for example, gelatin, gelatin derivatives, cellulose derivatives, polysaccharides such as dextran, gum arabic and the like; and synthetic polymeric substances such as water soluble polyvinyl compounds like poly(vinylpyrrolidone), acrylamide polymers and the like. Other synthetic polymeric compounds which can be employed include dispersed vinyl compounds such as in latex form and particularly those which increase dimensional stability of photothermographic materials. Suitable binders include polymers such as water insoluble polymers of alkyl acrylates or methacrylates and those which have cross-linking sites which facilitate hardening or curing as well as those having recurring sulfobetaine units. Especially suitable binding agents include high molecular weight materials and resins such as poly(vinyl butyral), cellulose acetate butyrate, poly(methyl methacrylate), poly(vinylpyrrolidone), ethyl cellulose, poly(styrene), poly(vinyl chloride), chlorinated rubber, poly(isobutylene), butadiene styrene copolymers, vinyl chloride-vinyl acetate copolymers, copolymers of vinyl acetate, vinyl chloride and maleic acid, poly(vinyl alcohol), and high molecular weight ethylene oxide polymers and active methylene polymers such as those described in U.S. Pat. No. 3,904,418 by Ponticello and Mowrey.

The photothermographic composition can be coated on a wide variety of supports. Useful supports include those which can withstand the processing temperatures employed such as cellulose ester film, poly(vinyl acetal) film, polystyrene film, poly(ethylene terephthalate) film, polycarbonate film and related films or resinous materials, as well as glass, paper, metal and the like. Typically a flexible support is employed.

Hardenable layers of a photothermographic element, as described, can be hardened by various organic or inorganic hardeners alone or in combination, such as aldehydes, ketones, vinyl sulfones, aziradines, mucochloric acid and the like which do not adversely affect the sensitometric properties of the photothermographic materials. Hardeners which cause adverse reduction of the described composition should be avoided.

The photothermographic elements and materials according to the invention can contain addenda and layers commonly employed in photothermographic elements, such as antistatic and/or conducting layers, plasticizers and/or lubricants, surfactants, matting agents, brightening agents, light-absorbing materials, filter dyes, antihalation dyes and absorbing dyes, and the like.

The various components of the photothermographic materials of the invention can be added from water solutions, or suitable organic solvent solutions can be used. The components can be added using various procedures known in the photographic art.

If desired, an agent, sometimes referred to as a toning agent or activator-toning agent, can be employed with the photothermographic materials according to the invention to provide an increase in density at certain processing temperatures. Suitable toning agents, also known as activator-toning agents, include cyclic imide toning agents such as phthalimide, N-hydroxyphthalimide, succinimide, and N-hydroxysuccinimide, and the like. These are described, for instance, in Belgian Pat. No. 766,590, issued June 15, 1971. Sulfolane in some instances can provide improved results in the described photothermographic compositions. Some photothermographic elements and compositions described according to the invention do not need a toning agent.

Spectral sensitizing dyes can be used conveniently to confer additional sensitivity to the light sensitive silver halide employed according to the invention. For instance, additional spectral sensitization can be obtained by treating the silver halide with a solution of a sensitizing dye in an organic solvent or the dye can be added in the form of a dispersion. Spectral sensitizers which can be used include the cyanines, merocyanines, complex-(trinuclear or tetranuclear) merocyanines, complex-(trinuclear or tetranuclear) cyanines, holopolar cyanines, styryls, hemicyanines, such as enamines, oxonols, and hemioxonols.

A range of concentrations of each component in the photothermographic material can be employed. Typically, each light sensitive layer of a photothermographic element according to the invention can comprise (a) from about 0 to about $1.0 \times 10^{-1}$ moles of silver as the described complex and (b) about $1.0 \times 10^{-3}$ to about $1.0 \times 10^{-2}$ moles of the described photosensitive silver halide per square meter of support and (c) a reducing agent in at least molar equivalency to conduct development based on reducible silver ions and up to 10 times equivalents in excess. An optimum concentration of each component will depend upon the particular components, the desired image, processing temperature and the like.

The bleachable dye can be added directly to the photothermographic composition prior to coating or can be added after the composition is applied to the support.

The photothermographic layer and/or other layers of a photothermographic element according to the invention can be coated by various coating procedures including dip coating, airknife coating, curtain coating or extrusion coating using hoppers of the type described in U.S. Pat. No. 2,681,294 of Beguin, issued June 15, 1954. If desired, two or more layers can be coated simultaneously by procedures known in the art.

The silver image on the photothermographic element can be produced after imagewise exposure within a short time by merely moderately overall heating the photothermographic element. For instance, a visible image on a photothermographic element according to the invention can typically be produced within a few seconds, e.g., about 1 to about 60 seconds after exposure by heating the element to a temperature within the range of about 100° C. to about 250° C., typically a temperature within the range of about 130° C. to about 180° C. Usually, the time of heating is less than about 20 seconds, such as about 2 to 5 seconds at a temperature of about 180° C. Optimum time of heating and optimum temperature of heating can be determined employing test procedures well known in the art.

One embodiment of the invention accordingly includes a method of developing and stabilizing an image in an exposed photothermographic element comprising a support having thereon (a) a reducing agent, as described, (b) a silver salt of a thione compound, also as described, (c) a photosensitive component consisting essentially of photosensitive silver halide, (d) a bleachable dye and, if desired, (e) a binder, comprising heating the photothermographic element to a temperature within the range of about 100° C. to about 250° C.

In developing an image in a photothermographic element according to the invention, increasing or decreasing the length of time of heating can enable use of a higher or lower temperature within the described range.

In some cases it may be convenient to produce the positive dye image using only a single heating step. This can be accomplished by placing a timing layer between the photothermographic element and the activating sheet and exposing and heat processing whereby the bleaching is delayed until the silver image is developed.

The activator sheet can also be preheated to a molten state prior to laminating to release excess moisture and prevent gas bubbles when the dry activator sheet is laminated to the silver dye image.

The invention is further illustrated by the following examples.

EXAMPLE 1

This is a comparative example.

A photographic silver halide element comprising a film support having coated thereon a layer containing:

| | |
|---|---|
| Silver chlorobromide emulsion | 40 mgAg/ft$^2$ (0.093m$^2$) |
| Chicago Blue azo dye | 40 mg/ft$^2$ |
| [structure: OCH$_3$, OH, NH$_2$, SO$_3$Na, N=N, SO$_3$Na]$_2$ | |
| Gelatin | 250 mg/ft$^2$ |
| Bis (vinylsulfonylmethyl) ether | 25 mg/ft$^2$ | was imagewise exposed to tungsten light to provide a latent image and developed for 1 minute at 23° C. in Kodak D-19 Developer, fixed, washed and dried. At this stage, the gelatinous layer of the photographic element contained a visible image in metallic silver and the uniformly distributed azo dye.

Separate samples of the developed photographic element were then laminated with a series of activator sheets identified below which had been preheated for 5 seconds at 100° C. Each activator sheet comprised a polyester support coated with a layer containing:

| | |
|---|---|
| Sulfonated polystyrene (polymeric vehicle) | 250 mg/ft$^2$ (0.093m$^2$) |
| 1,6-Hexanediol (thermal solvent) | 500 mg/ft$^2$ |
| Thiourea (complexing agent) | 500 mg/ft$^2$ |
| p-Toluenesulfonic acid (acid) | 500 mg/ft$^2$ |

| Activator No. |
|---|
| 1 - As above |
| 2 - Like 1 but also containing 1 mg/ft$^2$ K$_2$S$_2$O$_8$ |
| 3 - Like 1 but also containing 10 mg/ft$^2$ K$_2$S$_2$O$_8$ |
| 4 - like 1 but also containing 100 mg/ft$^2$ K$_2$S$_2$O$_8$ |

In each case, the activator sheet was employed in the process within 1 hour after preparation. The laminated samples were heated for approximately one minute by contact with a metal block having a temperature of 100° C. In the laminant employing Activator No. 1, a well-defined positive dye image was obtained. In the laminants employing Activator Nos. 2 through 4, the image discrimination decreased as the level of potassium persulfate increased, until at 100 mg/ft$^2$ persulfate (Activator No. 4) it was apparent that the silver image had been bleached but no dye had been imagewise destroyed.

In a second test, Activator No. 1 had been kept at room temperature for 33 days prior to lamination and processing as described above. Results similar to those produced with Activator No. 4 in the first test were obtained, indicating that the thiourea had been aerially oxidized on keeping.

EXAMPLE 2

A set of three activator sheets was prepared as in Example 1 except that the thiourea was replaced with equal amounts of the following complexing agents. Each sheet contained 100 milligrams potassium persulfate per square foot to simulate oxidation on keeping. The complexing agent in each sheet was:

| Activator No. | Complexing Agent |
|---|---|
| 5 | [structure: thiazoline with CH$_3$, =S, N-CH$_2$COOH] |
| 6 | [structure: thiazoline with CH$_3$, =S, N-CH$_2$CH$_2$COOH] |
| 7 | [structure: benzothiazoline, =S, N-CH$_2$CH$_2$COOH] |

Separate samples of each activator were then laminated to a predeveloped photographic element and heated as described in Example 1. In each sample, a well-defined positive dye image was obtained comparable to that obtained with Activator No. 1 (fresh) of Example 1, indicating that each complexing agent was resistant to oxidation.

EXAMPLE 3

Four activator sheets containing the complexing agents identified in the following table were prepared. The concentration of components is listed in mg/0.093 m$^2$.

| | Activator No. | | | |
|---|---|---|---|---|
| Components | 8 | 9 | 10 | 11 |
| p-Toluenesulfonic acid | 500 | 500 | 500 | 500 |
| 1,6-Hexanediol | 500 | 500 | 500 | 500 |
| Poly-N-vinylpyrrolidone | 250 | 250 | 250 | 250 |
| Thiourea | 500 | — | — | — |
| 4-Methylimidazolidine-2-thione | — | 500 | — | — |
| Tetramethylthiourea | — | — | 500 | — |
| 3-Carboxymethyl-4-methyl-4-thiazoline-2-thione | — | — | — | 500 |

A photographic element as described in Example 1, was exposed and predeveloped as described in Example 1. At this stage, the gelatinous layer of the photographic element contained a negative image in metallic silver and the uniformly distributed azo dye.

Separate samples of the element were then laminated with fresh samples of the above activator sheets and heated for 30 seconds at 100° C. Positive dye images appeared in each sample with essentially no dye density in the area of maximum silver development.

Additional samples of the activator sheets were then stored at room temperature for two weeks and the testing procedure was repeated employing the aged activators. It was apparent that Activator Nos. 8, 9 and 10 caused bleaching of the metallic silver image but a significant amount of dye was retained in Dmin areas, i.e., areas of maximum silver development. The results obtained with Activator No. 11 were identical to those obtained in the fresh tests, i.e., well-defined positive dye images with low Dmins. These results indicate that aerial oxidation had caused degradation of the complexing agents employed in Activators Nos. 8, 9 and 10 but had not degraded that of Activator No. 11.

EXAMPLES 4-6

Samples of developed photographic elements as prepared in Example 1 were laminated with a series of activator sheets as identified below. Each activator sheet comprised a polyester support coated with a layer containing 250 mg/0.093 m² sulfonated polystyrene, 500 mg/0.093 m² 1,6-hexanediol, 500 mg/0.093 m² p-toluenesulfonic acid and 500 mg/0.093 m² of the particular silver halide complexing agent used. The samples were laminated immediately after preparation of the activator sheet, after 7 days and after 14 days under conditions of 75° F. and 50% relative humidity. The results as determined by the methods of Examples 2 and 3 are shown in Table II.

Table II

| Example | Silver Halide Complexing Agent in the Activator | Dye Bleach Fresh | Dye Bleach 7 days | Dye Bleach 14 days | Occurrences of Aerial Oxidation Fresh | Occurrences of Aerial Oxidation 7 days | Occurrences of Aerial Oxidation 14 days |
|---|---|---|---|---|---|---|---|
| Control A | Thiourea | Very good | none | none | none | yes | yes |
| Control B | 4-methylimidazolidine-2-thione | " | some | " | " | slight | yes |
| Example 4 | ![structure with CH3, C=S, CH2-CH2-C(O)-CH3] | " | very good | very good | " | none | none |
| Example 5 | ![structure with CH3, C=S, CH2CH2COOH] | " | " | " | " | " | " |
| Example 6 | ![structure with CH3, C=S, CH3] | " | " | " | " | " | " |

In each of the examples, as described, the effective pH of the activator sheet was 4.0 or less.

The invention has been described in detail with particular reference to preferred embodiments thereof, but it will be understood that variations and modifications can be effected within the spirit and scope of the invention.

What is claimed is:

1. A silver dye-bleach process of thermally dye bleaching a photographic element comprising a silver image in association with a dye that is bleachable in a silver dye-bleach process comprising contacting said image with a dry, activator sheet comprising a support having thereon a layer or layers comprising
   (a) a non-volatile, diffusible acid selected from the group consisting of non-volatile, diffusible mineral acids and organic acids containing up to 10 carbon atoms,
   (b) a 3-substituted thiazoline, oxazoline, imidazoline or imidazolidine-2-thione silver halide complexing agent; and
   (c) a non-hydrolyzable polymeric vehicle
   wherein said sheet has an effective pH of up to 6.0 and is solid up to at least 50° C. with a melting point lower than 200° C.; and heating to a temperature within the range of about 50° C. to about 150° C. to laminate the sheet to the element and produce a dye image.

2. The process of claim 1 wherein the activator sheet also contains a non-hydrolyzable thermal solvent containing up to 10 carbon atoms.

3. The process of claim 1 wherein the bleachable dye is an azo dye.

4. The process of claim 1 wherein the activator sheet also contains a dye-bleach catalyst.

5. The process of claim 1 wherein the complexing agent has the structure

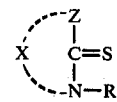

wherein Z is S, O or $NR^1$ and wherein R and $R^1$ are independently selected from the group consisting of an aliphatic organic radical and an aromatic organic radical; wherein neither R nor $R^1$ contains a terminal alcoholic OH group; X represents the atoms necessary to close a 5-membered unsaturated or saturated heterocyclic ring and wherein X can be aryl-substituted or fused to an aryl group; and, wherein said complexing agent contains a total of 20 carbon atoms or less.

6. The process of claim 1 wherein the mineral or organic acid is selected from the group consisting of sulfuric acid, acetic acid, citric acid, phenylphosphoric acid, phenylphosphonic acid, phenylphosphinic acid, para-toluenesulfonic acid, benzenesulfonic acid, and carboxylic acids containing up to 10 carbon atoms.

7. The process of claim 1 wherein the activator sheet also contains a non-hydrolyzable thermal solvent which is selected from the group consisting of poly(ethylene glycol), poly(ethylene oxide), decanediol and hexanediol.

8. The process of claim 1 wherein the activator sheet comprises from about 1.0 g/m² to about 50 g/m² of a mineral or organic acid, from about 1.0 g/m² to about 50 g/m² of a substituted heterocyclic thiazoline, oxazoline, imidazoline or imidazolidine silver halide complexing agent, and from about 1.0 g/m² to about 50 g/m² of a non-hydrolyzable polymeric vehicle.

9. A silver dye-bleach process of thermally dye bleaching a photographic element comprising a silver image in association with a dye that is bleachable in a silver dye-bleach process comprising contacting said image with a dry, activator sheet comprising a support having thereon a layer or layers comprising
  (a) a non-volatile, diffusible acid consisting essentially of para-toluenesulfonic acid,
  (b) a silver halide complexing agent consisting essentially of 3-carboxymethyl-4-methyl-4-thiazoline-2-thione, and
  (c) a non-hydrolyzable, polymeric vehicle consisting essentially of poly(vinylpyrrolidone),
wherein said layer or layers has an effective pH of up to 6.0 and is solid up to 50° C. with a melting point lower than 200° C.; and heating the resulting laminate to a temperature within the range of about 50° C. to about 150° C. to laminate the sheet to the element and produce a dye image.

10. A silver dye-bleach process of thermally dye bleaching a photographic element comprising a silver image in association with a dye that is bleachable in a silver dye-bleach process comprising contacting said image, in the absence of a silver dye-bleach catalyst, with a dry, activator sheet comprising a support having thereon a layer or layers comprising
  (a) a non-volatile, diffusible acid selected from the group consisting of non-volatile, diffusible mineral acids and organic acids containing up to 10 carbon atoms,
  (b) a 3-substituted thiazoline, oxazoline, imidazoline or imidazolidine-2-thione silver halide complexing agent; and
  (c) a non-hydrolyzable polymeric vehicle wherein said sheet has an effective ph of up to 6.0 and is solid up to at least 50° C. with a melting point lower than 200° C.; and heating to a temperature within the range of about 50° C. to about 150° C. to laminate the sheet to the element and produce a dye image.

11. The process of claim 10 wherein the activator sheet also contains a non-hydrolyzable thermal solvent containing up to 10 carbon atoms.

12. The process of claim 10 wherein the activator sheet also contains a non-hydrolyzable thermal solvent which is selected from the group consisting of poly(ethylene glycol), poly(ethylene oxide), decanediol and hexanediol.

13. The process of claim 10 wherein the complexing agent has the structure

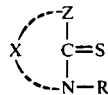

wherein Z is S, O or NR¹ and wherein R and R¹ are independently selected from the group consisting of an aliphatic organic radical and an aromatic organic radical; wherein neither R nor R¹ contains a terminal alcoholic OH group; X represents the atoms necessary to close a 5-membered unsaturated or saturated heterocyclic ring and wherein X can be aryl-substituted or fused to an aryl group; and, wherein said complexing agent contains a total of 20 carbon atoms or less.

14. The process as in claim 10 wherein the complexing agent consists essentially of 3-carboxymethyl-4-methyl-4-thiazoline-2-thione.

15. The process as in claim 10 wherein the mineral or organic acid is selected from the group consisting of sulfuric acid, acetic acid, citric acid, phenylphosphoric acid, phenylphosphonic acid, phenylphosphinic acid, para-toluenesulfonic acid, benzenesulfonic acid, and carboxylic acids containing up to 10 carbon atoms.

16. A silver dye-bleach process of thermally dye bleaching a photographic element comprising a silver image in association with a dye that is bleachable in a silver dye-bleach process comprising contacting said image, in the absence of a silver dye-bleach catalyst, with a dry, activator sheet comprising a support having thereon a layer or layers comprising
  (a) a non-volatile, diffusible acid consisting essentially of para-toluenesulfonic acid,
  (b) a silver halide complexing agent consisting essentially of 3-carboxymethyl-4-methyl-4-thiazoline-2-thione, and
  (c) a non-hydrolyzable, polymeric vehicle consisting essentially of poly(vinylpyrrolidone),
wherein said layer or layers has an effective pH of up to 4.0 and is solid up to 50° C. with a melting point lower than 200° C.; and heating the resulting laminate to a temperature within the range of about 50° C. to about 150° C. to laminate the sheet to the element and produce a dye image.

17. A silver dye-bleach process of thermally dye bleaching a photographic element comprising a silver image in association with a dye that is bleachable in a silver dye-bleach process comprising contacting said image with a dry, activator sheet comprising a support having thereon a layer comprising
  (a) a non-volatile, diffusible acid selected from the group consisting of phenylphosphonic acid, phenylphosphoric acid, phenylphosphinic acid, sulfuric acid, acetic acid, citric acid, para-toluenesulfonic acid, benzene sulfonic acid and carboxylic acids containing up to 10 carbon atoms,
  (b) a 3-substituted thiazoline, oxazoline, imidazoline or imidazolidine-2-thione silver halide complexing agent and
  (c) a non-hydrolyzable polymeric vehicle selected from the group consisting of poly(styrene sulfonic acid), poly(ethylene oxide), poly(acrylamide), poly(acrylic acid), poly(vinylpyrrolidone) and poly(vinyl alcohol) vehicles,
wherein said sheet has an effective pH up to 6.0 and is solid up to at least 50° C. with a melting point lower than 200° C.; and heating to a temperature within the range of about 50° C. to about 150° C. to laminate the sheet to the element and produce a dye image.

18. The process of claim 17 wherein the activator sheet also comprises a silver dye-bleach catalyst.

19. A silver dye-bleach process of thermally dye bleaching a photographic element comprising a silver image in association with a dye that is bleachable in a silver dye-bleach process comprising contacting said image, in the absence of a silver dye-bleach catalyst, with a dry, activator sheet comprising a support having thereon a layer comprising
  (a) a non-volatile, diffusible acid selected from the group consisting of phenylphosphonic acid, phenylphosphoric acid, phenylphosphinic acid, sulfuric acid, acetic acid, citric acid, para-toluenesulfonic acid, benzene sulfonic acid and carboxylic acids containing up to 10 carbon atoms, (b) a 3-substituted thiazoline, oxazoline, imidazoline or imidazolidine-2-thione silver halide complexing agent and (c) a non-hydrolyzable polymeric vehicle selected from the group consisting of poly(styrene sulfonic acid), poly(ethylene oxide), poly(acrylamide), poly(acrylic acid), poly(vinylpyrrolidone) and poly(vinyl alcohol) vehicles, wherein said sheet has an effective pH of up to 6.0 and is solid up to at least 50° C. with a melting point lower than 200° C.; and heating to a temperature within the range of about 50° C. to about 150° C. to laminate the sheet to the element and produce a dye image.

20. A heat developable, photographic element for a dry, thermal silver dye-bleach process comprising a support having thereon (A) a first layer comprising (1) photosensitive silver halide, (2) an image-forming combination comprising (i) an organic, silver salt oxidizing agent with (ii) a reducing agent, (3) a polymeric binder and (4) a dye that is bleachable in a silver dye-bleach process, and, contiguous to (A), a second layer comprising (a) a non-volatile, diffusible acid selected from the group consisting of phenylphosphonic acid, phenylphosphoric acid, phenylphosphinic acid, sulfuric acid, acetic acid, citric acid, para-toluenesulfonic acid, benzene sulfonic acid and carboxylic acids containing up to 10 carbon atoms, (b) a 3-substituted thiazoline, oxazoline, imidazoline or imidazolidine-2-thione silver halide complexing agent and (c) a non-hydrolyzable polymeric vehicle selected from the group consisting of poly(styrene sulfonic acid), poly(ethylene oxide), poly(acrylamide), poly(acrylic acid), poly(vinylpyrrolidone) and poly(vinyl alcohol) vehicles, wherein said second layer has an effective pH of up to 4.0 and is solid up to at least 50° C. with a melting point lower than 200° C.

21. A heat developable, photographic element for a dry, thermal silver dye-bleach process comprising, respectively, a support having thereon (A) a first layer comprising (1) photosensitive silver halide, (2) an image-forming combination comprising (i) an organic, silver salt oxidizing agent with (ii) a reducing agent, (3) a polymeric binder, and (4) a dye that is bleachable in a silver dye-bleach process, and, contiguous to (A), a second layer comprising (a) a non-volatile, diffusible acid selected from the group consisting of non-volatile, diffusible mineral acids and organic acids containing up to 10 carbon atoms;

(b) a 3-substituted thiazoline, oxazoline, imidazoline or imidazolidine-2-thione silver halide complexing agent; and (c) a non-hydrolyzable polymeric vehicle, wherein said second layer has an effective pH of up to 4.0 and is solid up to at least 50° C. with a melting point lower than 200° C.

22. A heat developable, photographic element as in claim 21 wherein the non-hydrolyzable polymeric vehicle is a member selected from the group consisting of poly(styrene sulfonic acid), poly(ethylene oxide), poly(acrylamide), poly(acrylic acid), poly(vinylpyrrolidone), and poly(vinyl alcohol).

23. A heat developable, photographic element for a dry, thermal silver dye-bleach process comprising, respectively, a support having thereon (A) a first layer comprising (1) photosensitive silver halide, (2) an image-forming combination comprising (i) an organic, silver salt oxidizing agent, (3) a polymeric binder, and (4) a dye that is bleachable in a silver dye-bleach process, and, contiguous to (A), a second layer comprising (a) a non-volatile, diffusible acid selected from the group consisting of non-volatile, diffusible mineral acids and organic acids containing up to 10 carbon atoms;

(b) a silver halide complexing agent having the structure

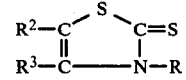

wherein R is an aliphatic radical containing from 1 to 12 carbon atoms which has a terminal acidic hydrogen atom bonded to an oxygen atom and salts thereof; $R^2$ and $R^3$ are independently selected from the group consisting of hydrogen, aliphatic radicals and phenyl; or, $R^2$ and $R^3$ taken together form a 6 to 12 carbon atom containing aromatic ring or a 5 to 7 member alicyclic ring, and (c) a non-hydrolyzable polymeric vehicle, wherein said second layer has an effective pH up to 4.0 and is solid up to at least 50° C. with a melting point lower than 200° C.

24. A heat developable, photographic element as in claim 23 wherein said complexing agent consists essentially of 3-carboxymethyl-4-methyl-4-thiazoline-2-thione.

* * * * *

UNITED STATES PATENT AND TRADEMARK OFFICE
CERTIFICATE OF CORRECTION

PATENT NO. : 4,168,169

DATED : September 18, 1979

INVENTOR(S) : Wilbert J. Humphlett and Rowland G. Mowrey

It is certified that error appears in the above-identified patent and that said Letters Patent are hereby corrected as shown below:

Column 4, line 46, "1,1,3-trimethyl-5carboxy-3-(p-" should read --- 1,1,3-trimethyl-5-carboxy-3-(p- ---.

Column 5, line 18, delete "equipment" and insert ---temperatures---; line 41, "portions" should read ---proportions---.

Column 7, line 2, "$CH_2CH_2COOCH_3$" should read --- $CH_2CH_2COCH_3$ ---.

Column 14, line 13, "Mclaen" should read ---McLaen---.

Column 15, line 19, "alkylen" should read ---alkylene---.

Column 23, line 40, "ph" should read ---pH---.

Signed and Sealed this

Ninth Day of December 1980

[SEAL]

Attest:

SIDNEY A. DIAMOND

Attesting Officer

Commissioner of Patents and Trademarks